US010214504B2

(12) United States Patent
Brendel et al.

(10) Patent No.: US 10,214,504 B2
(45) Date of Patent: Feb. 26, 2019

(54) PROCESS AND REACTOR FOR THE EPOXIDATION OF PROPENE

(71) Applicants: EVONIK DEGUSSA GMBH, Essen (DE); THYSSENKRUPP INDUSTRIAL SOLUTIONS AG, Essen (DE)

(72) Inventors: Marc Brendel, Bruchköbel (DE); Manfred Bärz, Freigericht (DE); Johannes Kowoll, Bochum (DE); David Bolz, Frankfurt (DE); Willi Hofen, Rodenbach (DE); Jürgen Schemel, Bad Soden (DE); Bernd Jaeger, Bickenbach (DE); Niels Bredemeyer, Waltrop (DE); Bärbel Kolbe, Witten (DE); Norbert Ullrich, Essen (DE); Michael Dopfer, Sulzbach (DE); Wolfgang Wöll, Maintal (DE); Peter Porscha, Kelkheim (DE); Dana Pfenning, Mannheim (DE); Maik Bernhard, Frankfurt (DE)

(73) Assignees: Evonik Degussa GmbH, Essen (DE); thyssenkrupp Industrial Solutions AG, Essen (DE)

( * ) Notice: Subject to any disclaimer, the term of this patent is extended or adjusted under 35 U.S.C. 154(b) by 0 days.

(21) Appl. No.: 15/778,318

(22) PCT Filed: Nov. 1, 2016

(86) PCT No.: PCT/EP2016/076273
§ 371 (c)(1),
(2) Date: May 23, 2018

(87) PCT Pub. No.: WO2017/089076
PCT Pub. Date: Jun. 1, 2017

(65) Prior Publication Data
US 2018/0370934 A1 Dec. 27, 2018

(30) Foreign Application Priority Data

Nov. 26, 2015 (EP) .................................... 15196549

(51) Int. Cl.
C07D 301/12 (2006.01)
C07D 303/04 (2006.01)
B01J 19/24 (2006.01)

(52) U.S. Cl.
CPC ........ C07D 301/12 (2013.01); B01J 19/2425 (2013.01); C07D 303/04 (2013.01); *B01J 2219/24* (2013.01)

(58) Field of Classification Search
CPC .. C07D 301/12; C07D 303/04; B01J 19/2425; B01J 2219/24
See application file for complete search history.

(56) References Cited

U.S. PATENT DOCUMENTS

| 4,308,409 | A | 12/1981 | Wu et al. |
| 5,274,140 | A | 12/1993 | Venturello et al. |
| 6,372,924 | B2 | 4/2002 | Thiele |
| 6,673,950 | B1 | 1/2004 | Teles et al. |
| 6,861,042 | B2 | 3/2005 | Korl et al. |
| 7,601,263 | B2 | 10/2009 | Ebert et al. |
| 7,658,893 | B2 | 2/2010 | Bassler et al. |
| 7,670,572 | B2 | 3/2010 | Porscha et al. |
| 7,833,498 | B2 | 11/2010 | Goebbel et al. |
| 7,863,211 | B2 | 1/2011 | Strebelle et al. |
| 8,545,673 | B2 | 10/2013 | Dietz et al. |
| 9,539,549 | B2 | 1/2017 | Haensel et al. |
| 10,100,024 | B2 | 10/2018 | Stochniol et al. |
| 10,125,108 | B2 | 11/2018 | Jahn et al. |
| 2003/0040637 | A1 | 2/2003 | Hofen et al. |
| 2006/0058539 | A1 | 3/2006 | Babler et al. |
| 2015/0007951 | A1 | 1/2015 | Dietz et al. |
| 2017/0210718 | A1 | 7/2017 | Stochinol et al. |
| 2018/0002299 | A1 | 1/2018 | Bolz et al. |
| 2018/0002300 | A1 | 1/2018 | Bolz et al. |
| 2018/0030010 | A1 | 2/2018 | Breitenbach et al. |

(Continued)

FOREIGN PATENT DOCUMENTS

| DE | 195 07 584 | 9/1996 |
| EP | 0 100 119 | 2/1984 |

(Continued)

OTHER PUBLICATIONS

International Search Report for PCT/EP2016/076273 filed Nov. 1, 2016.
Written Opinion of the International Searching Authority for PCT/EP2016/076273 filed Nov. 1, 2016.
International Preliminary Report on Patentability for PCT/EP2016/076273 filed Nov. 1, 2016.
Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).
Guojie, et al., "Factors Affecting Propylene Epoxidation Catalyzed by Reaction-Controlled Phase-Transfer Catalyst," *Chinese Journal of Catalysis* 26:1005-1010 (Nov. 2005).

(Continued)

*Primary Examiner* — Timothy R Rozof
(74) *Attorney, Agent, or Firm* — Law Office of: Michael A. Sanzo, LLC

(57) ABSTRACT

Propene is continuously reacted with hydrogen peroxide in a tube bundle reactor comprising a multitude of parallel reaction tubes in the presence of a titanium silicalite catalyst arranged as a fixed bed in the reaction tubes. A cooling jacket encloses the reaction tubes, which has a feed point for cooling medium near the entry of the reaction tubes, a withdrawal point for cooling medium near the end of the reaction tubes and at least one additional withdrawal point upstream of the withdrawal point near the end of the reaction tubes. Cooling medium is fed to the feed point for cooling medium, a part of the cooling medium is withdrawn at the at least one additional withdrawal point and the remainder exits at the withdrawal point near the end of the reaction tubes.

20 Claims, 2 Drawing Sheets

(56) References Cited

U.S. PATENT DOCUMENTS

| | | |
|---|---|---|
| 2018/0030011 A1 | 2/2018 | Stock et al. |
| 2018/0030012 A1 | 2/2018 | Stock et al. |
| 2018/0057473 A1 | 3/2018 | Stock et al. |
| 2018/0134676 A1 | 5/2018 | Jahn et al. |

FOREIGN PATENT DOCUMENTS

| | | |
|---|---|---|
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/141734 | 11/2008 |
| WO | WO 2011/063937 | 6/2011 |

OTHER PUBLICATIONS

Kaur, et al., "Poloxometalate-catalysed epoxidation of propylene with hydrogen peroxide: microemulsion versus biphasic process," *Catalysis Communications* 5(11): 709-713 (Nov. 2004).

Li, et al., "Influence of composition of heteropolyphophatotungstate catalyst on epoxidation of propylene," *Journal of Molecular Catalysis A: Chemical* 218(2):247-252 (Aug. 2004).

Luthra, et al., "Homogeneous phase transfer catalyst recovery and re-use using solvent resistant membranes," *Journal of Membrane Science* 201:65-75 (2002).

Venturello, et al., "A New, Effective Catalytic System for Epoxidation of Olefins by Hydrogen Peroxide under Phase-Transfer Conditions," *J. Org. Chem.* 483831-3833 (1983).

U.S. Appl. No. 15/329,626, filed Jan. 26, 2017, US-2017/0210718 A1, Jul. 27, 2017, Stochinol.

U.S. Appl. No. 15/570,167, filed Oct. 15, 2017, US-2018/0134676 A1, May 27, 2018, Jahn.

U.S. Appl. No. 15/778,337, filed May 23, 2018, Pascaly.

U.S. Appl. No. 15/778,425, filed May 23, 2018, Hofen.

U.S. Appl. No. 15/778,562, filed May 23, 2018, Wiederhold.

U.S. Appl. No. 16/070,873, filed Jul. 18, 2018, Schmidt.

Notice of Allowance dated Oct. 3, 2018 for copending U.S. Appl. No. 15/778,562.

PROCESS AND REACTOR FOR THE EPOXIDATION OF PROPENE

CROSS REFERENCE TO RELATED APPLICATIONS

The present application is US national stage of international application PCT/EP2016/076273, which had an international filing date of Nov. 1, 2016, and which was published in English on Jun. 1, 2017. Priority is claimed to European application EP 15196549.8, filed on Nov. 26, 2015.

FIELD OF THE INVENTION

The present invention relates to a process for the epoxidation of propene with hydrogen peroxide in the presence of a titanium silicalite fixed bed catalyst.

BACKGROUND OF THE INVENTION

The liquid phase epoxidation of propene with hydrogen peroxide in the presence of a titanium silicalite catalyst is known from EP 0 100 119 A1. The reaction is usually carried out with a fixed bed catalyst at a pressure of more than 10 bar to achieve high propene concentrations in the liquid phase reaction mixture. The epoxidation is highly exothermal and requires adequate temperature control, because excessive reaction temperatures lead to increased by-product formation which reduces product selectivity for propene oxide.

EP 0 659 473 A1 describes an epoxidation of propene with a titanium silicalite catalyst using a reactor having several adiabatic fixed beds, where liquid reaction mixture is withdrawn after each fixed bed, cooled in an external cooler and is partially returned to the entry of the respective fixed bed.

EP 1 247 806 A1 describes epoxidation of propene with a titanium silicalite catalyst in a cooled fixed bed reactor using a cooling medium having a minimum temperature of 40° C. and limiting the maximum temperature of the catalyst fixed bed to 60° C. Tubular or multi-tubular reactors having a cooling jacket are used for this purpose.

WO 2005/068062 describes epoxidation of propene with a titanium silicalite catalyst in a tube bundle reactor which has a multitude of parallel reaction tubes cooled with a common cooling jacket. The catalyst is arranged in the tubes and cooling medium is passed through the jacket space in co-current, entering the jacket space near the entry of the tubes where starting materials are fed and exiting the jacket space near the end of the tubes. Baffles may be arranged in the jacket space to guide the flow of cooling medium transvers to the reaction tubes in order to improve the heat transfer. The jacket space may be divided into several zones and different cooling media or cooling media of different temperature can be used in the separate zones. WO 2005/068062 teaches the use of helical reaction tubes instead of straight reaction tubes to achieve a more uniform heat removal from the tubes and to avoid hot spots.

SUMMARY OF THE INVENTION

It has now been found that cooling with co-current flow of the cooling medium in the jacket space of a tube bundle reactor as described in WO 2005/068062 does not provide a constant reaction temperature along the length of a reaction tube when carrying out the epoxidation of propene with a titanium silicalite catalyst fixed bed arranged in the reaction tube. There is always a temperature profile along the tube length with a maximum temperature near the inlet to the reaction tube and a significant temperature drop towards the end of the reaction tube.

It has further been found that a more even temperature profile along the tube length with smaller temperature differences can be achieved by withdrawing a part of the cooling medium from the jacket space at one or several points along the reaction tube, the remainder of the cooling medium exiting the jacket space near the end of the reaction tubes.

Subject of the invention is therefore a process for the epoxidation of propene by continuously reacting propene with hydrogen peroxide in the presence of a titanium silicalite catalyst in a tube bundle reactor comprising a multitude of parallel reaction tubes and a cooling jacket enclosing the reaction tubes, said cooling jacket having a feed point for cooling medium near the entry of the reaction tubes and a withdrawal point for cooling medium near the end of the reaction tubes, where the catalyst is arranged as a fixed bed in the reaction tubes, a mixture comprising propene and hydrogen peroxide is continuously introduced to the entry of the reaction tubes and a reaction mixture comprising propene oxide exits at the end of the reaction tubes, characterized in that the cooling jacket has at least one additional withdrawal point for cooling medium upstream of the withdrawal point for cooling medium near the end of the reaction tubes, cooling medium is fed to the feed point for cooling medium, a part of the cooling medium fed to said feed point is withdrawn at the at least one additional withdrawal point and the remainder exits at the withdrawal point near the end of the reaction tubes.

The invention also provides a tube bundle reactor for the continuous epoxidation of propene comprising a multitude of parallel reaction tubes and a cooling jacket enclosing the reaction tubes, said cooling jacket having a feed point for cooling medium near the entry of the reaction tubes and a withdrawal point for cooling medium near the end of the reaction tubes, characterized in that the cooling jacket has at least one additional withdrawal point for cooling medium upstream of the withdrawal point for cooling medium near the end of the reaction tubes.

DETAILED DESCRIPTION OF THE INVENTION

Figure 1:
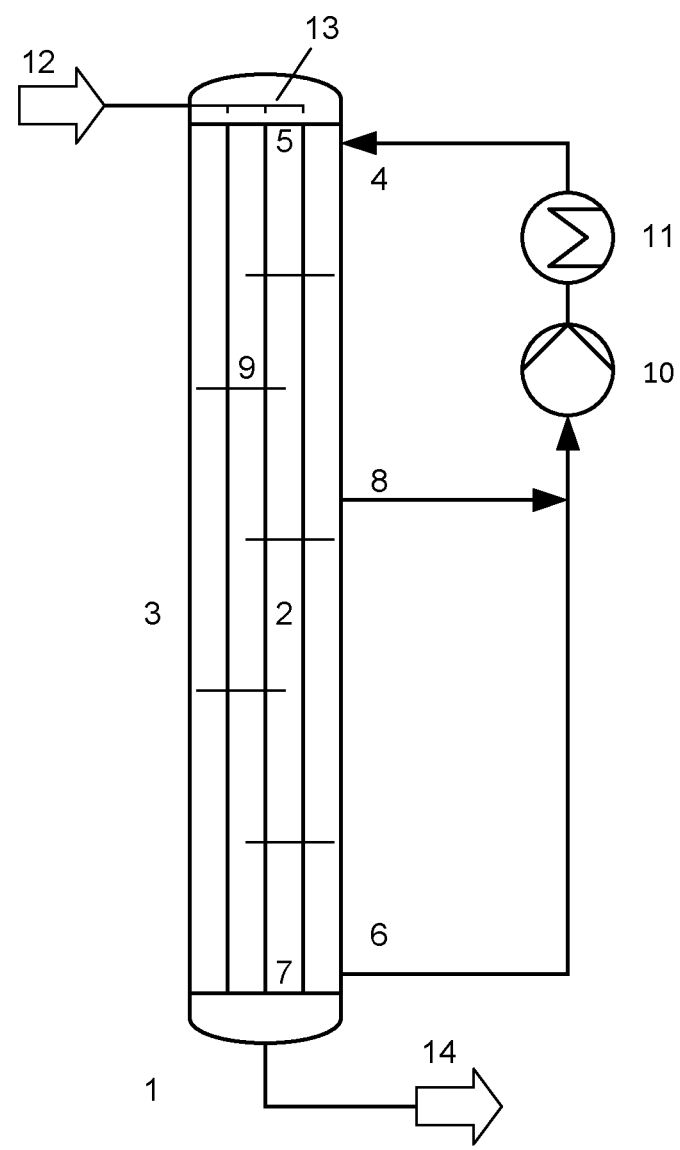
FIG. 1 shows a tube bundle reactor with a single additional withdrawal point for cooling medium, baffles arranged in the cooling jacket and a cooling medium circulated in a secondary cooling circuit.

The process of the invention is carried out in the tube bundle reactor of the invention which comprises a multitude of parallel reaction tubes and a cooling jacket enclosing the reaction tubes. The tube bundle reactor preferably comprises from 5000 to 20000 parallel reaction tubes, more preferably from 7500 to 15000 parallel reaction tubes. The reaction tubes preferably have a circular cross section with an internal diameter of preferably from 2 to 5 cm, more preferably from 2.5 to 4 cm. Preferably all reaction tubes of the tube bundle reactor have the same internal diameter. The reaction tubes preferably have a length of from 5 to 18 m, more preferably from 10 to 15 m.

The parallel reaction tubes are enclosed by a cooling jacket which has a feed point for cooling medium near the entry of the reaction tubes and a withdrawal point for cooling medium near the end of the reaction tubes. The feed point for cooling medium is preferably less than 1 m downstream from the entry of the reaction tubes and may be as close to the entry of the reaction tubes as technically possible. It may comprise several openings where cooling medium enters the cooling jacket within this distance from the entry of the reaction tubes. The withdrawal point for cooling medium is preferably less than 1 m upstream from the end of the reaction tubes and may be as close to the end of the reaction tubes as technically possible. It may comprise several openings where cooling medium is withdrawn from the cooling jacket within this distance from the end of the reaction tubes. The cooling jacket preferably comprises tube sheets at the entry of the reaction tubes and at the end of the reaction tubes, separating a reactor entry space connected to the entry of all parallel reaction tubes from the cooling jacket and separating a reactor exit space connected to the end of all parallel reaction tubes from the cooling jacket. The cooling jacket has at least one additional withdrawal point for cooling medium upstream of the withdrawal point for cooling medium near the end of the reaction tubes. The tube bundle reactor preferably has from 1 to 3 additional withdrawal points for cooling medium, more preferably 1 or 2 additional withdrawal points for cooling medium and most preferably a single additional withdrawal point for cooling medium. The at least one additional withdrawal point is preferably located at from 15 to 70% of the length of the reaction tubes, more preferably at from 18 to 50% of the length, the length being measured from the entry of the reaction tubes to the end of the reaction tubes. When the tube bundle reactor has several additional withdrawal points for cooling medium, they are preferably located at different lengths along the reaction tubes.

The tube bundle reactor of the invention preferably comprises baffles arranged in the cooling jacket transverse to the reaction tubes across part of the cross section of the cooling jacket for guiding cooling medium transverse to the reaction tubes. Each baffle preferably blocks from 10 to 30% of the cross section of the cooling jacket and neighboring baffles are preferably staggered to guide cooling medium transverse to the reaction tubes. The distance between baffles along the length of the reaction tubes is preferably from 10 to 40% of the average diameter of the cooling jackets. The baffles preferably have openings near or adjacent to the inner wall of the cooling jacket or a gap between the baffle and the inner wall of the cooling jacket. The number and size of the openings or the width of the gap is preferably chosen to provide a minimal flow rate within the entire volume of the cooling jacket and to avoid regions of stagnant cooling medium in nooks between a baffle and the cooling jacket.

The tube bundle reactor of the invention preferably comprises a secondary cooling circuit with at least one circulating pump and at least one heat exchanger for cooling the cooling medium with a primary coolant. The heat exchanger may be a liquid liquid heat exchanger for cooling with river water or sea water as primary coolant or an air cooler for cooling with air as primary coolant. The heat exchanger may also be a wet air cooler using evaporation of water into air for cooling the cooling medium.

In a preferred embodiment, the reactor of the invention has vertically arranged reaction tubes and comprises at least one distributor arranged above the entry of the reaction tubes, having openings for supplying liquid to each of the reaction tubes. The distributor preferably comprises separate openings for separately supplying two liquids to each of the reaction tubes, in particular for separately supplying a propene feed stream and a hydrogen peroxide feed stream to each of the reaction tubes. Suitable distributors are known from the prior art, for example from WO 2005/025716. This embodiment of the reactor is suitable for operating the process of the invention with trickle flow of liquid in the catalyst fixed bed.

The reactor of the invention may additionally comprise a phase separator arranged downstream of the end of the reaction tubes for separating liquid phases of a multi-phase reaction mixture exiting at the end of the reaction tubes. Suitable phase separators are known from the prior art, for example from WO 2008/141734.

The reactor of the invention preferably comprises temperature sensors arranged in the center of reaction tubes. Preferably, from 1 to 50 temperature sensors are used. Temperature sensors may be arranged in one or more rows within a corresponding number of reaction tubes. However, it is preferred to use separate temperature sensors in a corresponding number of reaction tubes.

Temperature sensors are preferably distributed within the tube bundle to monitor homogeneity of the temperature distribution within the tube bundle. Preferably, a set of temperature sensors is used within a reaction tube or in several reaction tubes at comparable locations within the tube bundle with the temperature sensors located at different distances along the length of the catalyst fixed bed, preferably at distances varying by 0.2 to 1.5 m, in order to monitor the temperature profile along the length of the catalyst fixed bed.

In the process of the invention, propene is continuously reacted with hydrogen peroxide in the presence of a titanium silicalite catalyst in the tube bundle reactor of the invention.

A mixture comprising propene and hydrogen peroxide is continuously introduced to the entry of the reaction tubes and a reaction mixture comprising propene oxide exits at the end of the reaction tubes. The propene may contain propane, preferably with a molar ratio of propane to propene of from 0.001 to 0.15 and more preferably of from 0.08 to 0.12. Hydrogen peroxide can be used as an aqueous solution, preferably containing from 30 to 75% by weight hydrogen peroxide and most preferably from 40 to 70% by weight.

The reaction is preferably carried out in a methanol solvent to provide a liquid mixture comprising propene, hydrogen peroxide and methanol. The methanol solvent can be a technical grade methanol, a solvent stream recovered in the work-up of the epoxidation reaction mixture or a mixture of both. The methanol solvent is preferably used in a weight ratio of 0.5 to 20 relative to the amount of aqueous hydrogen peroxide solution.

The reaction is carried out in the presence of a titanium silicalite catalyst which is arranged as a fixed bed in the reaction tubes. The titanium silicalite catalyst preferably has a MFI or MEL crystal structure. Most preferably a titanium silicalite 1 catalyst with MFI structure as known from EP 0 100 119 A1, is used. The titanium silicalite catalyst is preferably employed as a shaped catalyst in the form of granules, extrudates or shaped bodies. For the forming process the catalyst may contain 1 to 99% of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as fixed bed catalysts.

The catalyst fixed bed preferably extends over more than 70% of the length of the reaction tubes, more preferably over 90 to 98% of the length of the reaction tubes. In a preferred embodiment, a packing of inert material is arranged in the reaction tubes upstream of the catalyst fixed bed, preferably with a length of from 0.2 to 1.0 m. The inert material may be shaped in the same way or in a shape differing from the titanium silicalite catalyst. Preferred inert materials are glass beads. The packing of inert material provides an even distribution of flow and a mixing of liquid streams that are introduced separately into the reaction tubes before the mixture comprising propene and hydrogen peroxide enters the catalyst fixed bed.

The amount of catalyst employed and the rate at which the mixture comprising propene and hydrogen peroxide is introduced into the reaction tubes are preferably chosen to provide a hydrogen peroxide conversion of more than 90%, preferably at least 95%, upon passage of the mixture through the reaction tubes.

The reaction is preferably carried out at a pressure of at least 1.9 MPa using propene in excess to hydrogen peroxide. The pressure is preferably from 1.9 to 5.0 MPa, more preferably 2.1 to 3.6 MPa and most preferably 2.4 to 2.8 MPa. Propene is preferably used at a molar ratio of propene to hydrogen peroxide of from 1.1:1 to 30:1, more preferably 2:1 to 10:1 and most preferably 3:1 to 5:1. Using an excess of propene at a high pressure provides high reaction rate and hydrogen peroxide conversion and at the same time high selectivity for propene oxide.

The mixture comprising propene and hydrogen peroxide is preferably passed through the catalyst fixed bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) of from 1 to 20 $h^{-1}$, preferably 1.3 to 15 $h^{-1}$. It is particularly preferred to arrange the parallel reaction tubes vertically and pass a mixture comprising propene, hydrogen peroxide and methanol solvent through the reaction tubes in down-flow in trickle mode. Suitable conditions for maintaining the trickle mode during the epoxidation reaction are disclosed in WO 02/085873 on page 8 line 23 to page 9 line 15. Most preferably, the epoxidation reaction is carried out with the catalyst fixed bed maintained in a trickle mode at a pressure close to the vapor pressure of propene at the reaction temperature, using an excess of propene that provides a mixture comprising propene, hydrogen peroxide and methanol solvent, which mixture comprises two liquid phases, a first phase rich in propene and a second phase rich in methanol and hydrogen peroxide.

The reaction temperature is preferably from 20 to 80° C., more preferably from 25 to 60° C. Cooling medium is passed through the cooling jacket in order to remove the heat of reaction of the epoxidation reaction. The cooling medium is fed to the feed point for cooling medium near the entry of the reaction tubes, a part of the cooling medium fed to the feed point is withdrawn at at least one additional withdrawal point and the remainder exits at the withdrawal point near the end of the reaction tubes. The temperature and the amount of cooling medium fed to the feed point for cooling medium and the fraction of cooling medium withdrawn at the least one additional withdrawal point are adjusted to provide an even temperature distribution along the length of the catalyst fixed bed within a reaction tube. Preferably, the temperature distribution along the length of the catalyst fixed bed is adjusted to keep the reaction temperature along 70 to 98%, preferably along 80 to 95%, of the length of the catalyst fixed bed within a range of less than 5° C., preferably within a range of from 0.5 to 3° C. The temperature of the cooling medium fed to the feed point is preferably adjusted to a value 3 to 13° C. lower than the maximum temperature in the catalyst fixed bed. The fraction of cooling medium withdrawn at the least one additional withdrawal point is preferably from 10 to 70%, more preferably from 30 to 55%, when cooling medium is withdrawn at the least one additional withdrawal point. When the tube bundle reactor has several additional withdrawal points for cooling medium, cooling medium may be withdrawn at only one or at several additional withdrawal points at the same time and cooling medium may be withdrawn at different additional withdrawal points during the course of the reaction.

The cooling medium is preferably water and more preferably water circulated in a secondary cooling circuit. In a secondary cooling circuit, the temperature of the cooling medium is adjusted by cooling with water or air as a primary coolant in a separate heat exchanger. This separate heat exchanger may also be a wet air cooler using evaporation of water into air for cooling the cooling medium. The use of a secondary cooling circuit allows adjusting the temperature of the cooling medium even when the temperature of the primary coolant changes and allows the use of purified water as cooling medium to reduce corrosion of the cooling jacket and the outer wall of the reaction tubes.

Feeding of the cooling medium to a feed point near the entry of the reaction tubes and withdrawal of cooling medium downstream provides for co-current cooling which provides a decrease in heat transfer along the length of a reaction tube due to the decreasing temperature difference between the cooling medium and the reaction mixture inside the reaction tubes, matching the decrease in heat generated by the epoxidation along the length of a reaction tube due to the decrease in hydrogen peroxide concentration.

Compared to the use of a cooling jacket space with only one withdrawal point for cooling medium, the process of the invention provides a more even temperature distribution along the length of the catalyst fixed bed within a reaction tube and avoids the formation of a hot spot near the entry into the catalyst bed with a significant temperature drop along the catalyst fixed bed downstream of the hot spot.

Compared to the use of a cooling jacket space divided into several zones and the use of different cooling media or cooling media of different temperature as described in WO 2005/068062, the process of the invention requires less equipment and can use a reactor with a more simple construction. When a secondary cooling circuit is used, the process of the invention can be operated with a single circulation pump and a single cooler or cooling system for cooling the cooling medium of the secondary cooling circuit with a primary coolant, whereas the prior art cooling with different cooling media or cooling media of different temperature requires separate circulation pumps and heat exchangers for primary coolant for each zone of the divided cooling jacket.

Preferably, baffles are arranged in the cooling jacket transverse to the reaction tubes across part of the cross section of the cooling jacket, guiding cooling medium transverse to the reaction tubes, in order to improve the heat transfer from the reaction tubes to the cooling medium. The baffles preferably have openings near or adjacent to the inner wall of the cooling jacket or a gap between the baffle and the inner wall of the cooling jacket in order to provide a minimum flow rate within the entire volume of the cooling jacket and to avoid regions of stagnant cooling medium in nooks between the baffle and the cooling jacket.

The titanium silicalite catalyst gradually loses catalytic activity during the continuous epoxidation of propene with hydrogen peroxide and a fixed bed catalyst and therefore, the continuous epoxidation has to be interrupted from time to time to replace or regenerate the titanium silicalite catalyst. During such a run of the titanium silicalite catalyst, the temperature and the amount of cooling medium fed to the feed point for cooling medium and the fraction of cooling medium withdrawn at the least one additional withdrawal point are preferably adjusted to the decrease in catalyst activity. Preferably, the reaction temperature is increased during a run of the titanium silicalite catalyst in order to maintain sufficient conversion of hydrogen peroxide despite decreasing catalyst activity.

Cooling medium can be withdrawn at the additional withdrawal point throughout the entire run of the titanium silicalite catalyst or during part of such run. Preferably, no cooling medium is initially withdrawn at the additional withdrawal point until conversion of hydrogen peroxide decreases to a target value due to catalyst deactivation, followed by withdrawing an increasing part of the cooling medium at the additional withdrawal point to maintain an essentially constant conversion of hydrogen peroxide. In this context, essentially constant has the meaning that hydrogen peroxide conversion varies by no more than 2% at a given hydrogen peroxide feed. However, if the amount of hydrogen peroxide fed is changed to achieve a different production rate, hydrogen peroxide conversion may change by a larger value than 2%, but thereafter will be maintained within 2% of the new value. The withdrawal of cooling medium may be increased continuously or stepwise in steps of up to 10% of the amount of cooling medium fed. In a preferred embodiment, withdrawal of the cooling medium at the additional withdrawal point is increased until the fraction of cooling medium withdrawn at the additional withdrawal point reaches a target value, and thereafter the fraction of cooling medium withdrawn at the additional withdrawal point is kept within 0.8 to 1.2 times the target value and the temperature of the cooling medium is increased to maintain an essentially constant conversion of hydrogen peroxide. The target value for the fraction of cooling medium is preferably from 10 to 70%, more preferably from 30 to 55%. The temperature of the cooling medium can be increased continuously or stepwise in steps of up to 2° C., in order to keep the conversion of hydrogen peroxide within 90%, more preferably within 95% of the target value. Adjusting the fraction of cooling medium withdrawn at the additional withdrawal during a run of the titanium silicalite catalyst allows to maintain a narrow range of reaction temperature within the catalyst bed even when the catalyst activity starts to change along the length of the catalyst bed due to uneven deactivation of the catalyst along the length of the catalyst bed.

When, due to catalyst deactivation, the conversion of hydrogen peroxide falls below the desired level or the rise in reaction temperature necessary for maintaining the desired conversion of hydrogen peroxide leads to an undesired level of by-product formation, the continuous epoxidation is preferably interrupted to replace or regenerate the titanium silicalite catalyst. Preferably, the catalyst is regenerated within the reaction tubes. Regeneration within the reaction tubes can be achieved by methods known from the prior art, such as passing a gas stream at a temperature of from 200 to 600° C. through the catalyst fixed bed, passing a solvent stream through the catalyst bed or passing a solution of hydrogen peroxide through the catalyst bed in the absence of propene.

The titanium silicalite catalyst is preferably regenerated by passing a methanol solvent through the catalyst fixed bed at a temperature of from 100 to 200° C. for a period of 0.5 to 48 hours, more preferably 20 to 36 hours and most preferably 20 to 24 hours. The methanol solvent used for regenerating the catalyst preferably comprises more than 90% methanol and less than 10% water and more preferably more than 96 wt.-% methanol and less than 4% water. The methanol solvent is preferably a technical grade methanol, a solvent stream recovered in the work-up of the epoxidation reaction mixture or a mixture of both. The methanol solvent is preferably passed through the catalyst fixed bed in down flow mode and most preferably the flow rate is adjusted to maintain a trickle flow in the catalyst fixed bed. Regeneration may be performed at a constant temperature or using a temperature program. Passing the methanol solvent through the catalyst fixed bed is preferably started at the reaction temperature of the epoxidation reaction. The temperature is then raised to at least 100° C. and maintained at a temperature of at least 100° C. for the time necessary to carry out regeneration. Thereafter, the temperature is lowered back to the temperature used for epoxidation. Finally the methanol flow is stopped or the epoxidation is recommenced by starting to feed propene and hydrogen peroxide to the tube bundle reactor. In such a temperature program, raising and lowering of the temperature is preferably performed at a rate of from 5 to 30° C./h. During regeneration the pressure is adjusted to maintain the major part of the methanol solvent in the liquid state. The necessary pressure may be attained as the autogenous vapor pressure by evaporating part of the methanol solvent or by supplying an inert gas such as nitrogen. At least a part of the solvent that is passed through the catalyst fixed bed may be reused for regenerating the catalyst without prior purification. Preferably, the methanol solvent is passed through the catalyst fixed bed without reuse for a period of from 2% to 70% of the time used for regeneration and thereafter all the methanol solvent that is passed through the catalyst fixed bed is returned to the regeneration, creating a closed loop for washing the catalyst with a methanol solvent for the remainder of regeneration time. This reduces the amount of methanol needed for regenerating the catalyst.

The propene oxide formed by the epoxidation of propene can be separated from the reaction mixture exiting at the end of the reaction tubes by any method known from the prior art.

Preferably, the reaction mixture is subjected to a pressure reduction and propene vapor formed by the pressure reduction is recompressed and cooled to recover propene by condensation. The compressed propene vapor is preferably fed to a propene distillation column and separated into an overhead product comprising non-reacted propene and a bottoms product containing compounds having a boiling point higher than propene, such as propene oxide and methanol solvent. The overhead product comprising non-reacted propene can be recycled to the epoxidation reaction. The bottoms product can be combined with the liquid mixture remaining after the pressure reduction. The liquid mixture remaining after the pressure reduction is preferably separated by distillation in a pre-separation column to provide an overhead product comprising propene oxide, methanol and residual propene and a bottoms product comprising methanol, water and non-reacted hydrogen peroxide. The pre-separation column is preferably operated to provide an overhead product comprising from 20 to 60% of the methanol contained in the liquid phase of the last pressure reduction step. The pre-separation column preferably has from 5 to 20 theoretical separation stages in the stripping section and less than 3 theoretical separation stages in a rectifying section and is most preferably operated without reflux and without a rectifying section to minimize the residence time of propene oxide in the pre-separation column. The pre-separation column is preferably operated at a pressure of from 0.16 to 0.3 MPa. Propene oxide and methanol are condensed from the overhead product of the pre-separation column and propene is preferably stripped from the resulting condensate in a propene stripping column which provides a bottom stream comprising propene oxide and methanol which is essentially free of propene.

Propene oxide is preferably separated from the bottoms stream of the propene stripping column in an extractive distillation using water as the extraction solvent. The extractive distillation is preferably operated with additional feeding of a reactive compound containing an unsubstituted $NH_2$ group and capable of reacting with acetaldehyde during the extractive distillation, as described in WO 2004/048335. Extractive distillation with a reactive compound provides a high purity propene oxide containing less than 50 ppm of carbonyl compounds.

Methanol can be recovered from the bottoms product of the pre-separation column by distillation. Preferably, the bottoms product of the pre-separation column is subjected to a catalytic hydrogenation with hydrogen to remove non-reacted hydrogen peroxide remaining from step a), as described in WO 03/093255, before methanol is separated by distillation. Such catalytic hydrogenation reduces the amount of carbonyl compounds and acetals in the methanol separated by distillation, which is advantageous when the methanol is recycled to the reaction of step a). The bottoms product of the extractive distillation is preferably combined with the bottoms product of the pre-separation column, preferably before subjecting it to hydrogenation, in order to recover methanol. When hydrazine is used as the reactive compound in the extractive distillation, passing the bottoms product of the extractive distillation to the catalytic hydrogenation will convert non-reacted hydrazine and hydrazones formed from carbonyl compounds to ammonia and amines. The recovered methanol can be recycled as solvent to the epoxidation reaction. Preferably, the recovered methanol or the bottoms product of the pre-separation column, optionally combined with bottoms product of the extractive distillation and preferably after a catalytic hydrogenation, is treated to remove organic nitrogen compounds as described in WO 2004/048354, more preferably by subjecting it to an acid treatment. Most preferably, the recovered methanol is passed over a cation exchanger in the hydrogen form before it is recycled to the epoxidation reaction. Removal of organic nitrogen compounds, in particular amines, avoids deactivation of the titanium silicalite catalyst upon recycling of methanol.

FIG. 1 shows a tube bundle reactor with a single additional withdrawal point for cooling medium, baffles arranged in the cooling jacket and a cooling medium circulated in a secondary cooling circuit, which is preferably used for the process of the invention.

The tube bundle reactor (1) comprises a multitude of parallel reaction tubes (2) and a cooling jacket (3) enclosing the reaction tubes. The cooling jacket comprises tube sheets at the entry (5) of the reaction tubes and at the end (7) of the reaction tubes, separating a reactor entry space connected to the entry of all parallel reaction tubes from the cooling jacket and separating a reactor exit space connected to the end of all parallel reaction tubes from the cooling jacket. The cooling jacket further comprises a feed point (4) for cooling medium near the entry (5) of the reaction tubes, a withdrawal point (6) for cooling medium near the end (7) of the reaction tubes and an additional withdrawal point (8) for cooling medium upstream of the withdrawal point (6) for cooling medium near the end (7) of the reaction tubes. The cooling jacket also comprises baffles (9) arranged transverse to the reaction tubes across part of the cross section of the cooling jacket, which baffles are staggered along the length of the reaction tubes to guide cooling medium transverse to the reaction tubes. The baffles have a gap between the baffle and the inner wall of the cooling jacket to avoid regions of stagnant cooling medium. The cooling medium is circulated with a circulating pump (10) in a secondary cooling circuit and cooled with a heat exchanger (11) for primary coolant. A mixture (10) comprising propene and hydrogen peroxide is continuously introduced to the entry (5) of the reaction tubes through a distributor (13) and a reaction mixture (14) comprising propene oxide exits at the end (7) of the reaction tubes.

LIST OF REFERENCE SIGNS

1 Tube bundle reactor
2 Reaction tubes
3 Cooling jacket
4 Feed point for cooling medium
5 Entry of the reaction tubes
6 Withdrawal point for cooling medium
7 End of the reaction tubes
8 Additional withdrawal point for cooling medium
9 Baffles
10 Circulating pump
11 Heat exchanger for primary coolant
12 Mixture comprising propene and hydrogen peroxide
13 Distributor
14 Reaction mixture comprising propene oxide

EXAMPLES

Figure 2:
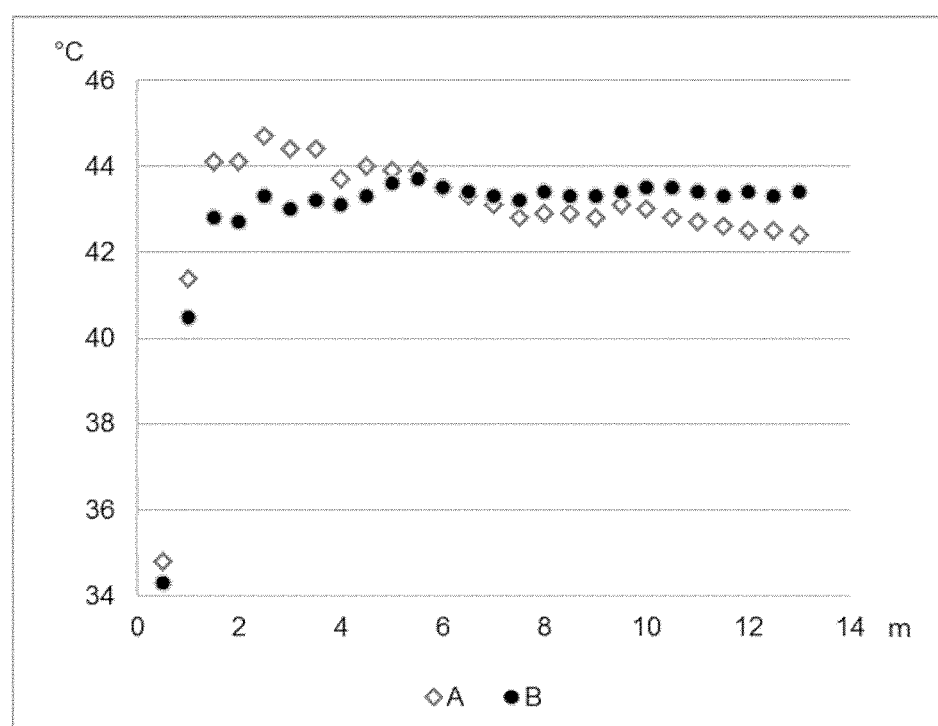
FIG. 2 shows temperature profiles along a reaction tube for withdrawing the entire cooling medium near the end of the reaction tube (profile A) and for withdrawing 33% of the cooling medium at a withdrawal point at 22% of the length of the reaction tube and the remainder near the end of the reaction tube (profile B).

Propene was epoxidized in a pilot plant reactor having a vertical single reaction tube of 13.4 m length enclosed by a cooling jacket. A row of temperature sensors was arranged in the center of the reaction tube with a distance of 0.5 m between individual temperature sensors. A catalyst fixed bed of an extruded titanium silicalite catalyst with a length of 12.8 m was placed in the reaction tube, starting at 0.6 m from the entry of the reaction tube. The pressure in the reactor was kept at 26 MPa by introducing nitrogen. A mixture comprising 40% by weight of propene, 11% by weight of a 70% by weight aqueous hydrogen peroxide solution and 49% by weight of methanol was fed to the top of the reaction tube and passed through the catalyst fixed bed in trickle mode. 225 kg/h cooling water were introduced into the cooling jacket at a feed point near the entry of the reaction tube and all of the cooling water exited the cooling jacket at a withdrawal point near the end of the reaction tube. After a stationary state was reached, the temperature profile A shown in FIG. 2 (temperature in ° C. vers. distance along the reaction tube in m) was measured with the temperature sensors. The temperatures in the center of the catalyst fixed bed measured from 1.5 m downstream the reaction tube to the end of the reaction tube were within a range of from 42.4 to 44.7° C. with a maximum difference of 2.3° C.

The experiment was then continued withdrawing 75 kg/h cooling water at a withdrawal point 3 m downstream the reaction tube and the remaining 150 kg/h at the withdrawal point near the end of the reaction tube. After a stationary state was reached, the temperature profile B shown in FIG. 2 was measured with the temperature sensors. The temperatures in the center of the catalyst fixed bed measured from 1.5 m downstream the reaction tube to the end of the reaction tube were within a range of from 42.7 to 43.7° C. with a maximum difference of 1.0° C.

The example demonstrates that withdrawing part of the cooling medium at the additional withdrawal point provides a more even temperature distribution along the length of the catalyst fixed bed compared to withdrawing all of the cooling medium near the end of the reaction tube.

The invention claimed is:

1. A process for the epoxidation of propene by continuously reacting propene with hydrogen peroxide in the presence of a titanium silicalite catalyst in a tube bundle reactor, wherein:
  a) the tube bundle reactor comprises a multitude of parallel reaction tubes and a cooling jacket enclosing the reaction tubes, said cooling jacket having a feed point for cooling medium near the entry of the reaction tubes and a withdrawal point for cooling medium near the end of the reaction tubes;
  b) the catalyst is arranged as a fixed bed in the reaction tubes, wherein a mixture comprising propene and hydrogen peroxide is continuously introduced to the entry of the reaction tubes and a reaction mixture comprising propene oxide exits at the end of the reaction tubes;
  c) the cooling jacket has at least one additional withdrawal point for cooling medium, upstream of the withdrawal point for cooling medium near the end of the reaction tubes, wherein:
    i) cooling medium is fed to the feed point for cooling medium;
    ii) a part of the cooling medium fed to said feed point is withdrawn at the at least one additional withdrawal point; and
    iii) the remainder of the cooling medium fed to said feed point exits at the withdrawal point near the end of the reaction tubes.

2. The process of claim 1, wherein the at least one additional withdrawal point is located at from 15 to 70% of the length of the reaction tubes.

3. The process of claim 1, wherein from 10 to 70% of the cooling medium fed is withdrawn at the at least one additional withdrawal point.

4. The process of claim 2, wherein from 10 to 70% of the cooling medium fed is withdrawn at the at least one additional withdrawal point.

5. The process of claim 1, wherein the cooling medium is water circulated in a secondary cooling circuit.

6. The process of claim 1, wherein baffles are arranged in the cooling jacket transverse to the reaction tubes across part of the cross section of the cooling jacket, guiding cooling medium transverse to the reaction tubes, said baffles having openings near or adjacent to the inner wall of the cooling jacket or a gap between the baffle and the inner wall of the cooling jacket.

7. The process of claim 6, wherein the at least one additional withdrawal point is located at from 15 to 70% of the length of the reaction tubes.

8. The process of claim 6, wherein from 10 to 70% of the cooling medium fed is withdrawn at the at least one additional withdrawal point.

9. The process of claim 1, wherein initially no cooling medium is withdrawn at the additional withdrawal point until conversion of hydrogen peroxide decreases to a target value due to catalyst deactivation, followed by withdrawing an increasing part of the cooling medium at the additional withdrawal point to maintain an essentially constant conversion of hydrogen peroxide.

10. The process of claim 9, wherein withdrawal of cooling medium at the additional withdrawal point is increased until the fraction of cooling medium withdrawn at the additional withdrawal point reaches a target value, and thereafter the fraction of cooling medium withdrawn at the additional withdrawal point is kept within 0.8 to 1.2 times the target value and the temperature of the cooling medium is increased to maintain an essentially constant conversion of hydrogen peroxide.

11. The process of claim 1, wherein the parallel reaction tubes are arranged vertically and a mixture comprising propene, hydrogen peroxide and methanol solvent is passed through the reaction tubes in down-flow in trickle mode.

12. The process of claim 11, wherein the at least one additional withdrawal point is located at from 15 to 70% of the length of the reaction tubes.

13. The process of claim 11, wherein from 10 to 70% of the cooling medium fed is withdrawn at the at least one additional withdrawal point.

14. The process of claim 11, wherein baffles are arranged in the cooling jacket transverse to the reaction tubes across part of the cross section of the cooling jacket, guiding cooling medium transverse to the reaction tubes, said baffles having openings near or adjacent to the inner wall of the cooling jacket or a gap between the baffle and the inner wall of the cooling jacket.

15. The process of claim 11, wherein the mixture comprising propene, hydrogen peroxide and methanol solvent comprises two liquid phases, a first phase rich in propene and a second phase rich in methanol and hydrogen peroxide.

16. The process of claim 1, wherein propene is reacted with hydrogen peroxide at a temperature of from 20 to 80° C. and a pressure of from 1.9 to 5.0 MPa.

17. A tube bundle reactor for the continuous epoxidation of propene comprising a multitude of parallel reaction tubes and a cooling jacket enclosing the reaction tubes, said cooling jacket having a feed point for cooling medium near the entry of the reaction tubes and a withdrawal point for cooling medium near the end of the reaction tubes, wherein the cooling jacket has at least one additional withdrawal point for cooling medium, upstream of the withdrawal point for cooling medium near the end of the reaction tubes.

18. The tube bundle reactor of claim 17, wherein the at least one additional withdrawal point is located at from 15 to 70% of the length of the reaction tubes.

19. The tube bundle reactor of claim 17, wherein baffles are arranged in the cooling jacket transverse to the reaction tubes across part of the cross section of the cooling jacket for guiding cooling medium transverse to the reaction tubes, said baffles having openings near or adjacent to the inner wall of the cooling jacket or a gap between the baffle and the inner wall of the cooling jacket.

20. The tube bundle reactor of claim 19, wherein the at least one additional withdrawal point is located at from 15 to 70% of the length of the reaction tubes.

* * * * *